(12) United States Patent
Dauster et al.

(10) Patent No.: US 9,901,378 B2
(45) Date of Patent: Feb. 27, 2018

(54) SURGICAL INSTRUMENTATION FOR SPINAL SURGERY

(75) Inventors: Andrew Dauster, Breinigsville, PA (US); Fabian Hoefer, Tuttlingen (DE)

(73) Assignee: AESCULAP AG (DE)

( * ) Notice: Subject to any disclaimer, the term of this patent is extended or adjusted under 35 U.S.C. 154(b) by 733 days.

(21) Appl. No.: 13/558,777

(22) Filed: Jul. 26, 2012

(65) Prior Publication Data

US 2013/0030445 A1  Jan. 31, 2013

Related U.S. Application Data

(60) Provisional application No. 61/513,152, filed on Jul. 29, 2011.

(51) Int. Cl.
 *A61B 17/70* (2006.01)

(52) U.S. Cl.
 CPC ........ *A61B 17/708* (2013.01); *A61B 17/7076* (2013.01); *A61B 17/7085* (2013.01); *A61B 17/7091* (2013.01)

(58) Field of Classification Search
 CPC .................................. A61B 17/7074–17/7092
 USPC .......................................... 606/99, 104, 86 A
 See application file for complete search history.

(56) References Cited

U.S. PATENT DOCUMENTS

| | | | | |
|---|---|---|---|---|
| 3,964,364 A * | 6/1976 | Poe | ................................ | 411/43 |
| 4,007,516 A * | 2/1977 | Coules | ......................... | 411/349 |
| 4,085,651 A * | 4/1978 | Koscik | ............................ | 411/43 |
| 4,602,496 A * | 7/1986 | Wagener | ..................... | 72/409.17 |
| 5,323,664 A * | 6/1994 | Fairfield et al. | .............. | 74/551.3 |
| 5,499,985 A * | 3/1996 | Hein et al. | ....................... | 606/99 |
| 6,045,309 A * | 4/2000 | LeVey | .............................. | 411/45 |
| 6,063,090 A | 5/2000 | Schlapfer | | |
| 6,183,472 B1 * | 2/2001 | Lutz | ............................. | 606/86 A |
| 6,540,461 B1 * | 4/2003 | Hawang | ......................... | 411/48 |

(Continued)

FOREIGN PATENT DOCUMENTS

AU       2003287273 A1    6/2004
AU       2003287273 B2    6/2004

(Continued)

OTHER PUBLICATIONS

International Application Serial No. PCT/US2012/048266, International Search Report and Written Opinion dated Nov. 15, 2012.

(Continued)

*Primary Examiner* — Matthew Lawson
*Assistant Examiner* — Amy Sipp
(74) *Attorney, Agent, or Firm* — Ratnerprestia

(57) ABSTRACT

An instrument assembly includes a downtube having a tubular body with a proximal end and a distal end. In one embodiment, the proximal end forms an opening for receiving a surgical tool, and the distal end forms at least two attachment members for attaching to a bone anchor. The tubular body forms a hollow passage extending from the proximal end to the distal end. The assembly includes a key for insertion into the proximal end of the downtube to attach the downtube to a bone anchor. The key includes an engagement end configured to engage the at least two attachment members when the key is inserted into the downtube. The key is rotatable within the tubular body between a clamping orientation and a releasing orientation.

18 Claims, 12 Drawing Sheets

(56) References Cited

U.S. PATENT DOCUMENTS

| | | | |
|---|---|---|---|
| 7,491,218 B2 | 2/2009 | Landry | |
| 8,496,706 B2* | 7/2013 | Ragab et al. | 623/17.11 |
| 8,636,740 B2* | 1/2014 | Weaver et al. | 606/86 A |
| 2004/0172022 A1 | 9/2004 | Landry | |
| 2005/0123379 A1* | 6/2005 | Barina et al. | 411/508 |
| 2005/0131408 A1 | 6/2005 | Sicvol | |
| 2005/0192579 A1* | 9/2005 | Jackson | 606/72 |
| 2006/0036244 A1* | 2/2006 | Spitler et al. | 606/61 |
| 2006/0074418 A1* | 4/2006 | Jackson | 606/61 |
| 2006/0074421 A1* | 4/2006 | Bickley et al. | 606/72 |
| 2006/0084993 A1 | 4/2006 | Landry | |
| 2006/0095035 A1 | 5/2006 | Jones | |
| 2006/0111715 A1* | 5/2006 | Jackson | 606/61 |
| 2006/0142761 A1 | 6/2006 | Landry | |
| 2006/0247658 A1 | 11/2006 | Pond | |
| 2007/0219554 A1 | 9/2007 | Landry | |
| 2007/0239159 A1 | 10/2007 | Altarac | |
| 2007/0239279 A1* | 10/2007 | Francis | 623/17.16 |
| 2007/0260246 A1 | 11/2007 | Biedermann | |
| 2008/0039838 A1 | 2/2008 | Landry | |
| 2008/0039840 A1* | 2/2008 | Songer et al. | 606/61 |
| 2008/0045956 A1* | 2/2008 | Songer et al. | 606/61 |
| 2008/0045957 A1 | 2/2008 | Landry | |
| 2008/0077139 A1 | 3/2008 | Landry | |
| 2008/0154277 A1* | 6/2008 | Machalk et al. | 606/99 |
| 2008/0215100 A1 | 9/2008 | Matthis | |
| 2009/0012567 A1 | 1/2009 | Biedermann | |
| 2009/0157125 A1* | 6/2009 | Hoffman et al. | 606/86 A |
| 2009/0171391 A1* | 7/2009 | Hutton et al. | 606/246 |
| 2009/0228053 A1 | 9/2009 | Kolb | |
| 2009/0318972 A1* | 12/2009 | Jackson | A61B 17/7037 606/264 |
| 2010/0036443 A1* | 2/2010 | Hutton et al. | 606/86 R |
| 2011/0077690 A1* | 3/2011 | Shin et al. | 606/278 |
| 2011/0278487 A1* | 11/2011 | King | 251/315.16 |
| 2012/0031792 A1* | 2/2012 | Petit | 206/438 |
| 2013/0018419 A1* | 1/2013 | Rezach et al. | 606/264 |
| 2014/0094917 A1* | 4/2014 | Salerni | 623/17.16 |
| 2014/0316468 A1* | 10/2014 | Keiser et al. | 606/252 |

FOREIGN PATENT DOCUMENTS

| | | |
|---|---|---|
| AU | 2005305193 A1 | 5/2006 |
| AU | 2008276119 A1 | 1/2009 |
| AU | 2009201461 A1 | 5/2009 |
| AU | 2003287273 C1 | 1/2010 |
| CA | 2502571 A1 | 5/2004 |
| CA | 2586554 A1 | 5/2006 |
| DE | 29806563 U1 | 6/1998 |
| DE | 10157814 A1 | 6/2003 |
| EP | 1558157 | 5/2004 |
| EP | 1835860 | 5/2006 |
| EP | 2 301 458 A1 | 3/2011 |
| JP | 2007513744 | 5/2007 |
| JP | 2007514512 | 6/2007 |
| JP | 2011514830 | 5/2011 |
| WO | 9825534 | 6/1998 |
| WO | 2005058141 | 6/2005 |
| WO | 2005058141 A2 | 6/2005 |
| WO | 2005058386 | 6/2005 |
| WO | WO-2009055026 A1 | 4/2009 |
| WO | 2009114422 | 9/2009 |

OTHER PUBLICATIONS

International Preliminary Report on Patentability and Written Opinion issued in International Application No. PCT/US2012/048266, dated Feb. 13, 2014.

German Search Report issued in related German Application No. 10 2011 053 295.1, dated May 8 2012 (with English language description of category codes).

International Application Serial No. PCT/US2012/048266, International Search Report dated Sep. 13, 2012, 6 pgs.

Japanese Office Action for Japanese Application No. 2014527549, dated Jun. 7, 2016 with translation, 7 pages.

* cited by examiner

SURGICAL INSTRUMENTATION FOR SPINAL SURGERY

CROSS REFERENCE TO RELATED APPLICATIONS

This application claims the benefit of priority under 35 U.S.C. § 119 to U.S. Application Ser. No. 61/513,152, filed Jul. 29, 2011, the contents of which are incorporated by reference herein and for all purposes.

FIELD

The present invention relates generally to surgical instrumentation, and more specifically to minimally invasive instruments and methods for providing access to a surgical site through a small incision.

BACKGROUND

Polyaxial screw assemblies are often used in spine fixation to stabilize the lumbar spine and promote bony fusion. Polyaxial screw assemblies can also be used as a possible anchor point for a dynamic system. In both approaches, the polyaxial screw assembly is implanted by establishing access through a posterior approach to the thoraco-lumbar spine. Many posterior procedures are done with an open surgical method, meaning that the skin of the patent is incised from the cranial aspect of the area to be treated to the caudal aspect. This can require a significantly long incision, potentially resulting in trauma to the muscles, nerves and other soft tissue of the back. This trauma can lead to biomechanical instability, greater possible necrosis, and an increased time for recovery.

Minimally invasive surgery (MIS) attempts to minimize the damage that the insertion of these implants causes through the use of smaller incisions and muscle splitting rather than cutting. The smallest footprint of the MIS family is referred to as percutaneous surgery, characterized by stab incisions for the introduction of the screw into the patient. MIS surgery in general, and percutaneous surgery in particular, make use of instruments called "downtubes", which can be looked at as temporary extensions of the screw body that communicate from the surgical site through to the surface of the skin. These tubes are removed once the surgery is complete.

Despite their advantages, conventional downtubes have a number of drawbacks. Many conventional downtubes fail to securely engage the screw body and remain in place during a procedure. In addition, conventional downtubes often feature a number of movable or sliding parts that are interconnected. Movable or sliding parts can make operation more complicated, and can be prone to binding and jamming with other parts.

Downtubes with multiple parts also create burdens prior to surgery, because the parts must be disassembled so that they can be cleaned and sterilized thoroughly prior to being used. Multiple parts also tend to increase the overall footprint size of the downtube, which is undesirable in minimally invasive procedures. Moreover, downtubes become more costly to manufacture as the number of parts increases. More parts generally require more manufacturing steps, increasing the probability of manufacturing error. In addition, parts can be lost during reprocessing of devices made from multiple components.

Given the drawbacks of known downtubes, there is a need for an improved downtube that is easier to use, less prone to complications, and less costly to manufacture.

SUMMARY

The drawbacks of conventional downtubes are resolved in many respects by instrument assemblies in accordance with the invention.

In one embodiment, a minimally invasive instrument assembly for providing access to a bone anchor includes a downtube having a tubular body with a proximal end and a distal end. The proximal end may form an opening for receiving a surgical tool, and the distal end may form at least two attachment members for attaching to a bone anchor. The tubular body may form a hollow passage extending from the proximal end to the distal end. The assembly may further include a key for insertion into the proximal end of the downtube to attach the downtube to a bone anchor. The key may include an engagement end configured to engage the at least two attachment members when the key is inserted into the downtube. The key may be rotatable within the tubular body between a clamping orientation, in which the at least two attachment members are separated from one another by a first distance, and a releasing orientation, in which the at least two attachment members are separated from one another by a second distance greater than the first distance.

BRIEF DESCRIPTION OF THE DRAWINGS

The foregoing summary and the following detailed description will be better understood in conjunction with the drawing figures, of which.

DETAILED DESCRIPTION

Figure 1:
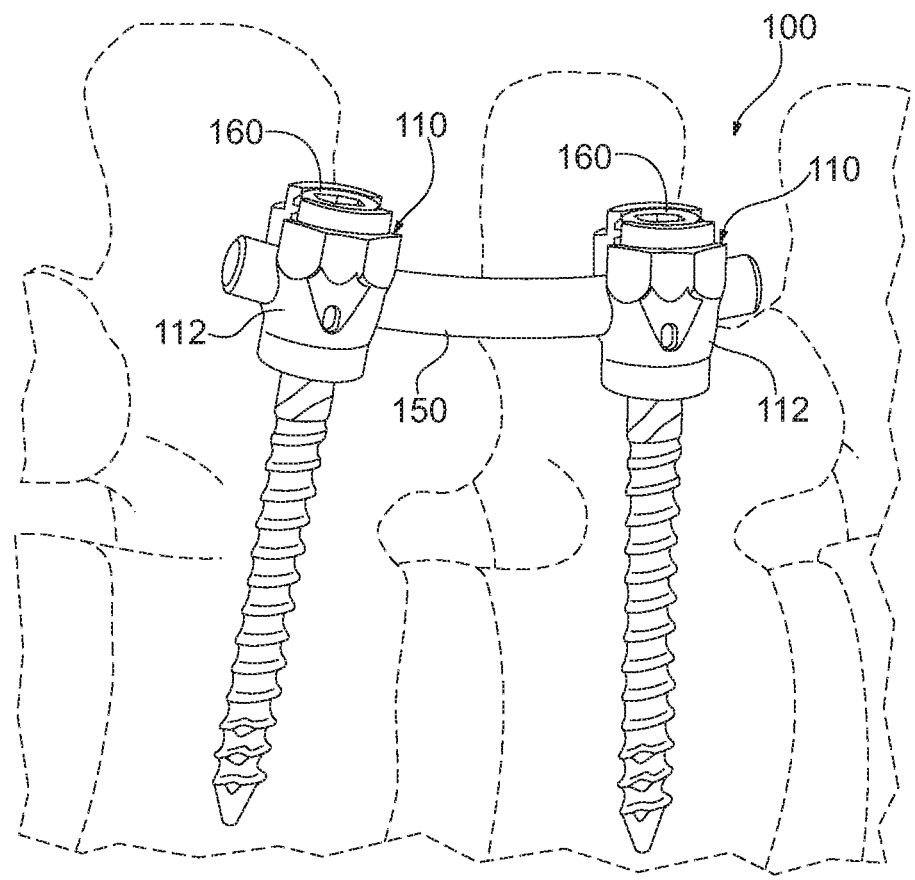
FIG. 1 is a perspective view of screw and rod fixation assembly for use in accordance with one embodiment of the invention.

Although the invention is illustrated and described herein with reference to specific embodiments, the invention is not intended to be limited to the details shown. Rather, various modifications may be made in the details within the scope and range of equivalents of the claims and without departing from the invention.

Instrument assemblies in accordance with the invention feature a downtube that is preferably formed as a unitary, one-piece instrument. A one-piece design has several advantages over conventional downtube designs. In particular, the one-piece design provides simplicity of operation by minimizing the number of parts, and avoids the use of moving components that can create complications during surgery. In addition, the one-piece design is ideal for cleaning and sterilization, because it requires no disassembly of parts prior to cleaning. Moreover, the one-piece construction allows for a smaller downtube footprint, providing greater stability in a small footprint area. The one-piece construction also makes the downtube stiffer than a similarly-sized downtube composed of multiple sliding or telescoping parts. Lastly, the single piece downtube is far more cost effective to manufacture than downtubes composed of multiple parts. The one-piece construct reduces the number of manufacturing and assembly steps, thereby reducing the chances for manufacturing error.

In one embodiment, an instrument assembly for providing access to a bone anchor includes:

an downtube having a tubular body with a proximal end and a distal end, the proximal end forming an opening for receiving a surgical tool, and the distal end forming at least two attachment members for attaching to a surgical implant or fastener, such as a bone anchor, the tubular body forming a hollow passage extending from the proximal end to the distal end; and a key for insertion into the proximal end of the downtube to attach the downtube to a bone anchor, the key comprising an engagement end, the engagement end configured to engage the at least two attachment members when the key is inserted into the downtube, the key rotatable within the tubular body between a clamping orientation, in which the at least two attachment members are separated from one another by a first distance, and a releasing orientation, in which the at least two attachment members are separated from one another by a second distance greater than the first distance.

Each of the at least two attachment members may include an arm having a bearing surface facing into the passage of the downtube. Each arm may include a tab extending inwardly into the passage. The tabs may be diametrically opposed to one another and may be circular.

The passage formed in the tubular body may be formed in a circular shape or a non-circular shape, including but not limited to a polygonal shape, an eccentric shape or an elliptical shape. The engagement end of the key may also be formed in a non-circular shape, including but not limited to a polygonal shape, an eccentric shape or an elliptical shape. The key may include a shaft with at least one tab extending radially outwardly from the shaft. The proximal end of the tubular body may include a slot adapted to receive the at least one tab on the key. The key may be rotatable within the tubular body when the tab is positioned in the slot, the slot limiting movement of the tab to limit rotation of the key within the tubular body between the clamping position and the releasing position.

The proximal end of the tubular body may include a threaded section with an outer thread. A slot may extend through the threaded section of the proximal end. The instrument assembly may further include a screwdriver. The screwdriver may include a shaft and a hollow knob that circumscribes the shaft. The knob may be rotatable relative to the shaft of the screwdriver and include an inner thread configured to engage the outer thread on the tubular body to connect the screwdriver to the downtube in a coaxial relationship. The tubular body may also include a hexagonal shaped midsection configured for engagement with a counter-torque instrument.

The instrument assembly may further include a rod persuader that includes a pair of pusher members and a hollow knob that circumscribes the pusher members. The knob may be rotatable relative to the pusher members and include an inner thread configured to engage the outer thread on the tubular body to connect the rod persuader to the downtube with the pusher members extending inside the tubular body. The rod persuader may include a central opening between the pusher members.

The instrument assembly may further include a set screw inserter, the set screw inserter including a shaft configured for insertion into the central opening of the rod persuader while the rod persuader is inserted into the tubular body. The set screw inserter may include a distal end and a set screw releasably attached to the distal end.

The examples provided in this description are directed to instrument assemblies that are used with bone anchors. It is contemplated that the instruments and methods in accordance with the invention can be used in many different applications, with many different types of implants, and are not limited exclusively to use with bone anchors. Moreover, instruments and methods described herein can be used, in minimally invasive procedures, such as percutaneous applications, or in open surgeries. The examples provided in this description are in no way limiting examples.

Figure 2:
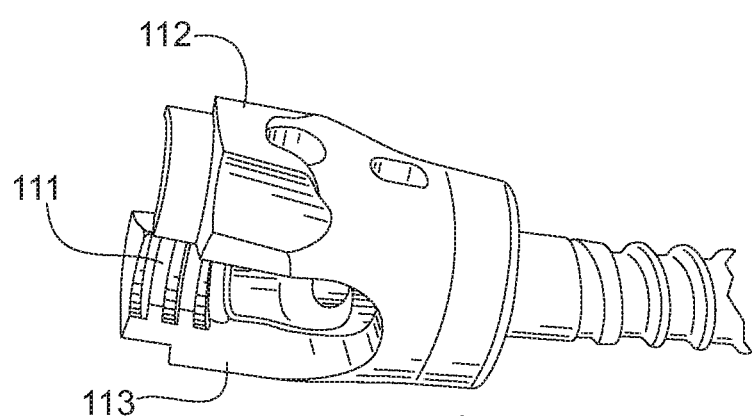
FIG. 2 is a perspective view of a screw assembly used in the assembly in FIG. 1.

FIGS. 1 and 2 illustrate one example of a screw and rod fixation system 100. Fixation system 100 includes two surgical screw assemblies 110. Each screw assembly 110 has a saddle-shaped head 112 forming a threaded opening 111 and a channel 113 for receiving an elongated fixation member or rod 150, as shown. Rod 150 is locked into the screw assemblies 110 by set screws 160 which are screwed into the threaded openings 111 of the heads 112 after the rod is properly positioned in each of the heads.

Figure 3:
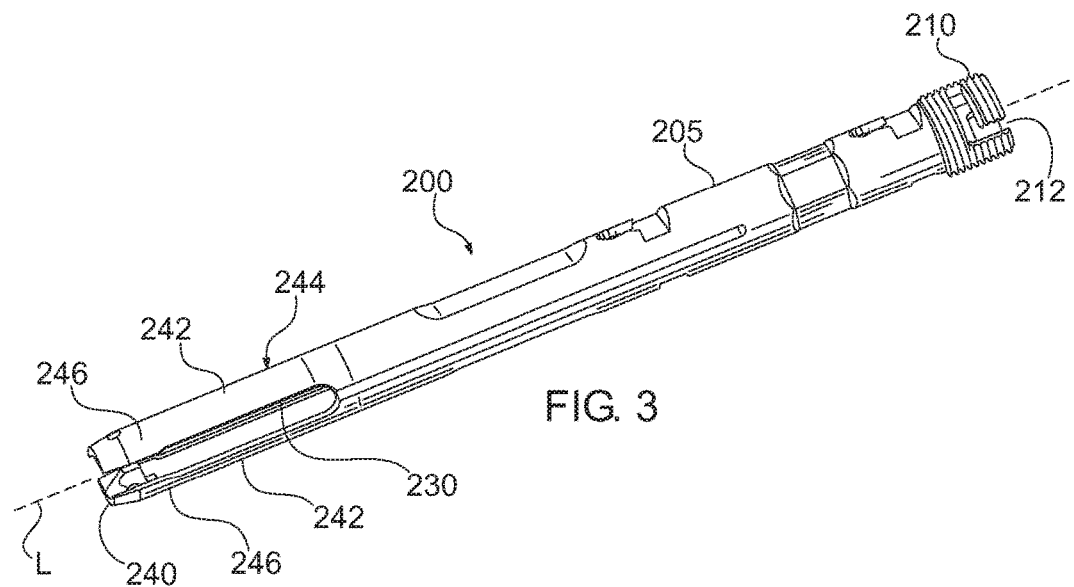
FIG. 3 is a perspective view of a downtube in accordance with one exemplary embodiment of the invention.

The rod 150 and set screws 160 are introduced into the screw assemblies 110 by means of a downtube. As noted above, downtubes function as temporary extensions for screw assemblies, forming a conduit to the surgical site. FIG. 3 shows one example of a downtube 200 in accordance with the invention. Downtube 200 includes a hollow tubular body 205 having a proximal end 210, a distal end 240 opposite the proximal end, and a hollow passage 230 extending between the proximal end and distal end. Proximal end 210 forms an opening 212 sized to receive other instrumentation, which will be described in more detail below. The distal end 240 includes a pair of attachment members 242 for attaching to the screw assemblies 110. It should be understood that the downtube can work with many types of bone anchors, including but not limited to the screw assemblies described and shown in the drawing figures.

The attachment members 242 collectively form a clamping mechanism 244 that securely attaches the downtube 200 to screw assemblies. Clamping mechanism 244 works by elastic deformation of the attachment members. Downtubes in accordance with the invention may be assembled from multiple parts formed of different materials. Nevertheless, preferred downtubes in accordance with the invention are constructed as one single homogeneous body of material, rather than an assembly of parts. The material selected for the homogeneous body preferably provides elastic properties at the attachment members. In addition, the material is preferably a biocompatible material. Suitable materials include but are not limited to stainless steel, plastics or superelastic shape memory alloys like Nitinol.

Figure 4:
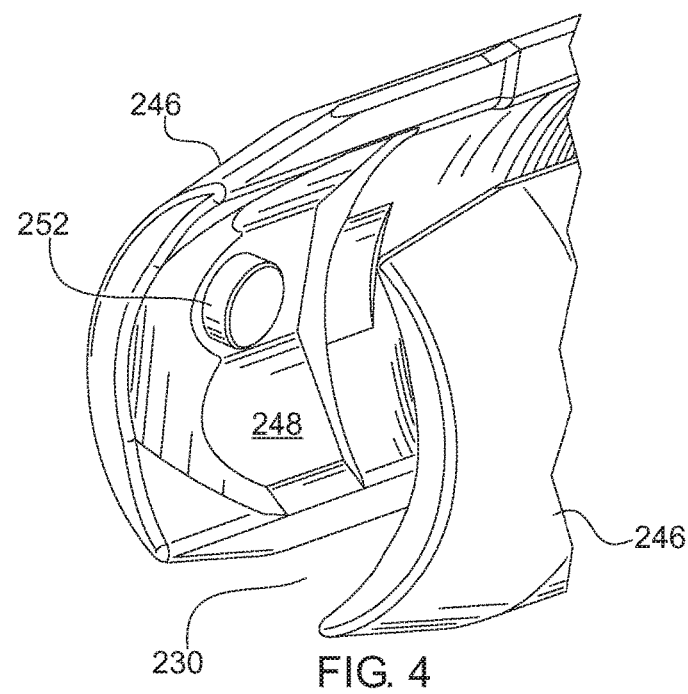
FIG. 4 is an enlarged truncated perspective view of the distal end of the downtube in FIG. 3.
Figure 5:
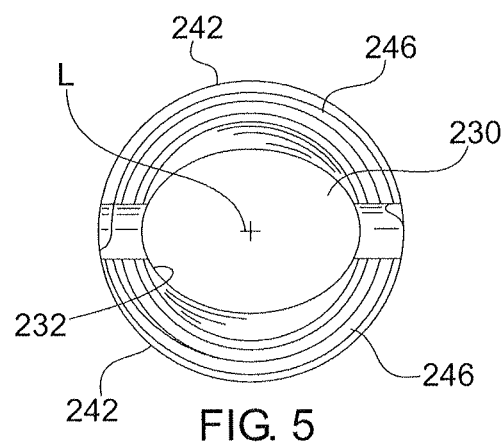
FIG. 5 is an end view of the downtube in FIG. 3.
Figure 6:
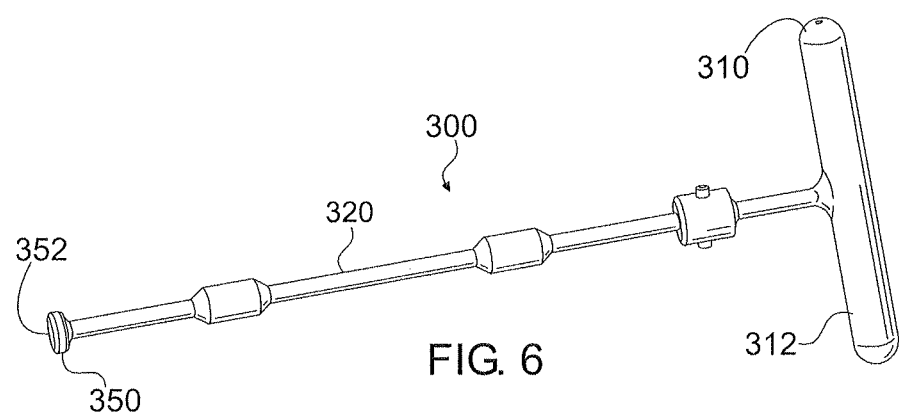
FIG. 6 is a perspective view of a key instrument for use with the downtube in FIG. 3.
Figure 7:
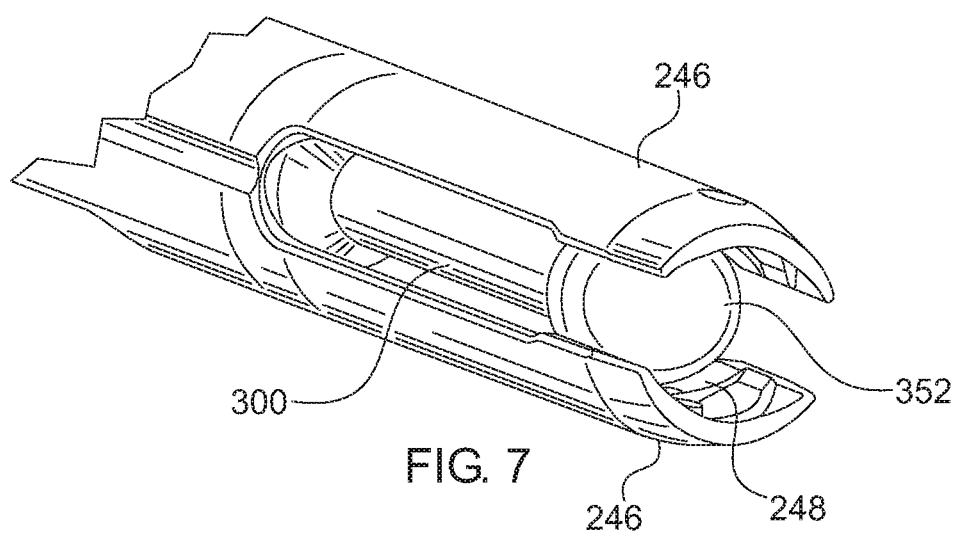
FIG. 7 is an enlarged truncated perspective view of the distal end of the downtube in FIG. 3, with the key instrument in FIG. 6 inserted inside the downtube.
Figure 8:
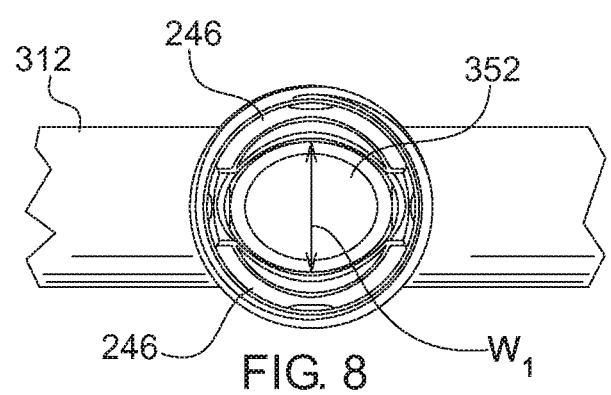
FIG. 8 is a truncated end view of the downtube in FIG. 3, with the key instrument in FIG. 6 inserted inside the downtube in a first orientation.

Each attachment member 242 includes an arm 246 having a bearing surface 248 facing into passage 230. Each bearing surface 248 includes an engagement element for attachment to a screw assembly 110. A variety of engagement elements can be used, including but not limited to bosses or detents, which may be fixed or deflectable. In the case of deflectable elements, the elements may be spring biased to project into passage 230, and retractable against the spring bias into the arms. In FIGS. 3 and 4, downtube 200 includes two engagement elements in the form of fixed circular tabs 252, one of which is visible in the drawings. Tabs 252 extend radially inwardly into passage 230 and are diametrically opposed to one another.

Clamping mechanism 244 is operable by opening or spreading apart the arms 246, so that a screw assembly 110 can be placed between the arms. The arms 246 are then closed or clamped together to securely connect downtube 200 to the screw assembly 110. Arms 246 are deflectable relative to one another between an "open" condition, in which the arms are spread apart by a first distance, and a "closed" condition, in which the arms are spread apart by a second distance which is smaller than the first distance.

Passage 230 has a section between the attachment members 242 with a cross sectional profile that facilitates opening and closing of the arms 246. Referring to FIGS. 5-9, passage 230 is shown with an elliptical shaped section 232 between arms 246. Arms 246 are deflected from the closed condition to the open condition, and vice versa, by inserting a "key" 300 into the elliptical shaped section 230 and rotating the key about a longitudinal axis L of downtube 200. Key 300 has a proximal end 310, a distal end 350, and a shaft 320 extending between the proximal end and distal end. Proximal end 310 includes a handle 312 in the form of a T-bar. Distal end 350 includes an engagement end 352 having an elliptical shape. The major and minor axes of the ellipse defining the shape of engagement end 352 may be proportional to the major and minor axes of the ellipse defining the shape of elliptical shaped section 232 in passage 230.

Once inserted into elliptical shaped section 232 of passage 230, the engagement end 352 is rotatable between a "clamping orientation" and a "releasing orientation". The key 300 is rotated 90 degrees about its longitudinal axis to move the key between the clamping orientation and releasing orientation. In the clamping orientation, shown in FIG. 8, the major axis of engagement end 352 is parallel to the major axis of elliptical shaped section 232. In a preferred embodiment, the width $W_1$ of engagement end 352 across the minor axis is more or less equal to the spacing between arms 246 in their relaxed state. As such, engagement end 352 does not deflect the arms apart in the clamping orientation.

Figure 9:
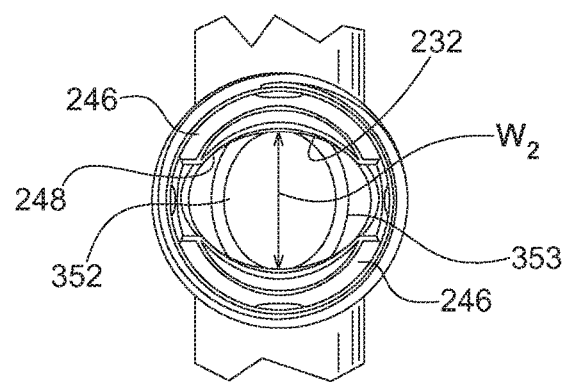
FIG. 9 is a truncated end view of the downtube in FIG. 3, with the key instrument in FIG. 6 inserted inside the downtube in a second orientation.
Figure 10:
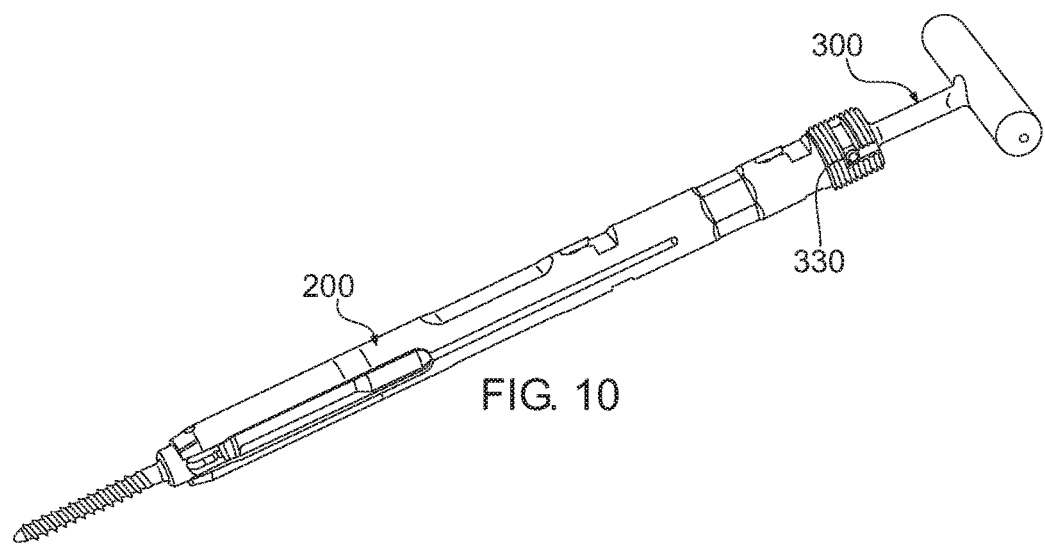
FIG. 10 is a perspective view of the downtube in FIG. 3 clamped onto a screw assembly, with the key instrument in FIG. 6 inside the downtube.
Figure 11:
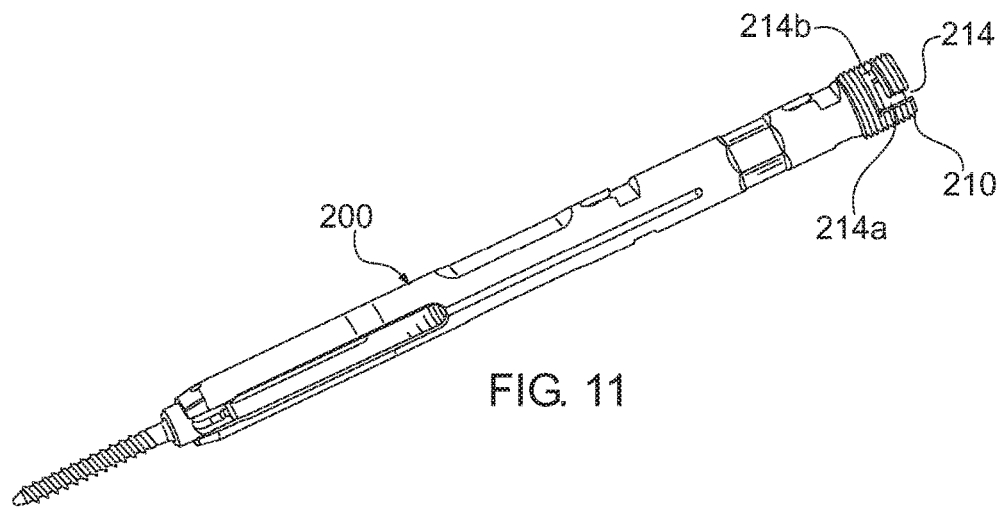
FIG. 11 is a perspective view of the downtube and screw assembly in FIG. 10, with the key instrument removed from the downtube.

In the releasing orientation, shown in FIG. 9, the major axis of engagement end 352 is parallel to the minor axis of elliptical shaped section 232. The width $W_2$ of engagement end 352 across its major axis is greater than the spacing between arms 246 in their relaxed state. Therefore, the edge 353 of engagement end 352 bears against the bearing surfaces 248 of the arms 246, spreading apart the arms in an outward direction to the open position. In the open position, the arms 246 are deflected outwardly under stored energy. When key 300 is subsequently rotated toward the clamping orientation, the bearing surfaces 248 of the arms 246 slide along the edge 353 of engagement end 352 and gradually converge or collapse toward one another. The resilience in arms 246 causes the arms to collapse or move toward one another until the arms are positioned in their relaxed state.

Figure 23:
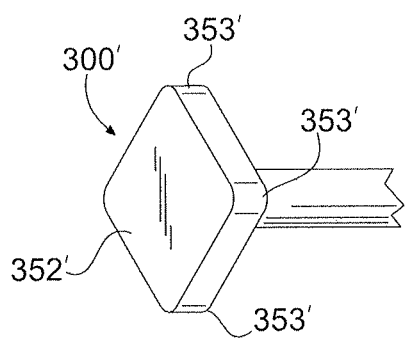
FIG. 23 is an enlarged truncated perspective view of a key instrument in accordance with another exemplary embodiment.

Although the engagement end 352 and passage 230 are shown with elliptical shapes, it will be understood that other geometries may also be used to facilitate the opening and closing of arms 246. The engagement ends and passages in accordance with the invention may feature any combination of geometrical configurations that cooperate to convert rotational displacement of the key into radial expansion of the downtube arms. For example, the passage and/or engagement end may have non-circular shapes, including but not limited to corresponding oval shapes, regular polygonal shapes and irregular polygonal shapes. With regard to regular polygonal shapes, the passage and/or engagement end may feature triangular, square, pentagonal, hexagonal, heptagonal or octagonal geometries. Referring to FIG. 23, a key 300' is shown with a diamond shaped engagement end 352' To facilitate smooth rotation, the corners 353' of the diamond on the engagement end 352' are rounded. The corresponding passage in the downtube could have a diamond shaped perimeter identical to or slightly larger than the diamond shape of engagement end 352'.

Figure 24:
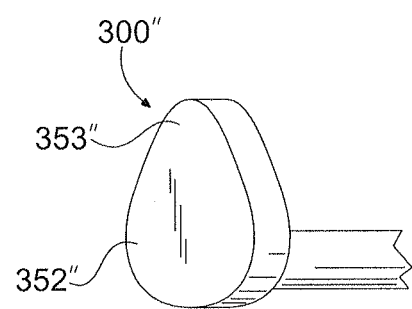
FIG. 24 is an enlarged truncated perspective view of a key instrument in accordance with another exemplary embodiment.

In other embodiments, the passage could have a rounded shape, and the engagement end could have an irregular or eccentric shape. For example, the engagement end could have a central portion and one or more lobes that extend outwardly from the central portion. Each lobe would act as a cam to deflect at least one of the arms outwardly when the lobe rotates into alignment with the bearing surface of an arm and bears against the arm. Referring to FIG. 24, for example, a key 300" is shown with an engagement end 352" having an eccentric lobe portion 353". Engagement end 352" is designed to rotate inside a circular passage of a downtube. Lobe portion 353" is configured to engage a bearing surface inside an arm of the downtube to deflect the arm radially outwardly as engagement end 352" rotates and the lobe radially aligns with the bearing surface.

Figure 25:
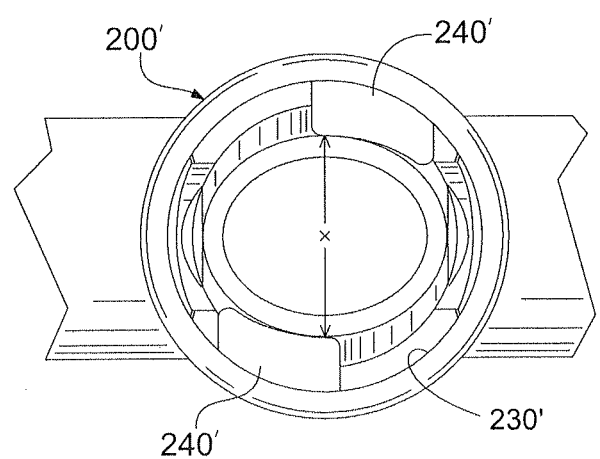
FIG. 25 is an end view of a down tube and key instrument in accordance with another exemplary embodiment.

Referring to FIG. 25, a downtube 200' is shown in accordance with another exemplary embodiment. Downtube 200' functions similarly to downtube 200. Instead of an elliptical shaped passage, however, downtube 200' features a circular passage 230' with a pair of hubs 240' extending into the passage. Hubs 240' project into passage 230' toward one another to form a constriction that reduces the width in direction X as shown. When engagement end 352 of key 300 is inserted into passage 230' and rotated with its minor axis parallel to direction X, the engagement end assumes a clamping orientation. That is, the engagement end 352 does not deflect the downtube arms, and the arms remain in a relaxed state as shown. When engagement end 352 is rotated with its major axis parallel to direction X, the engagement end assumes a releasing orientation, in which the engagement end deflects and spreads the downtube arms radially outwardly.

Figure 12A:
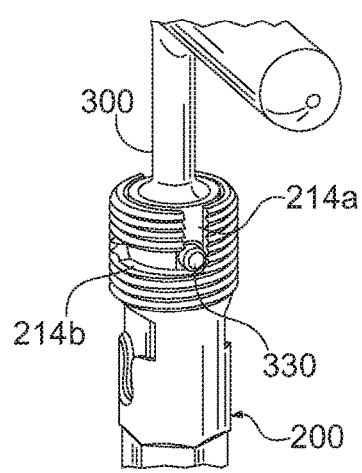
FIG. 12A is a truncated perspective view of the key instrument of FIG. 6 inserted into the downtube of FIG. 3 in a first position.
Figure 12B:
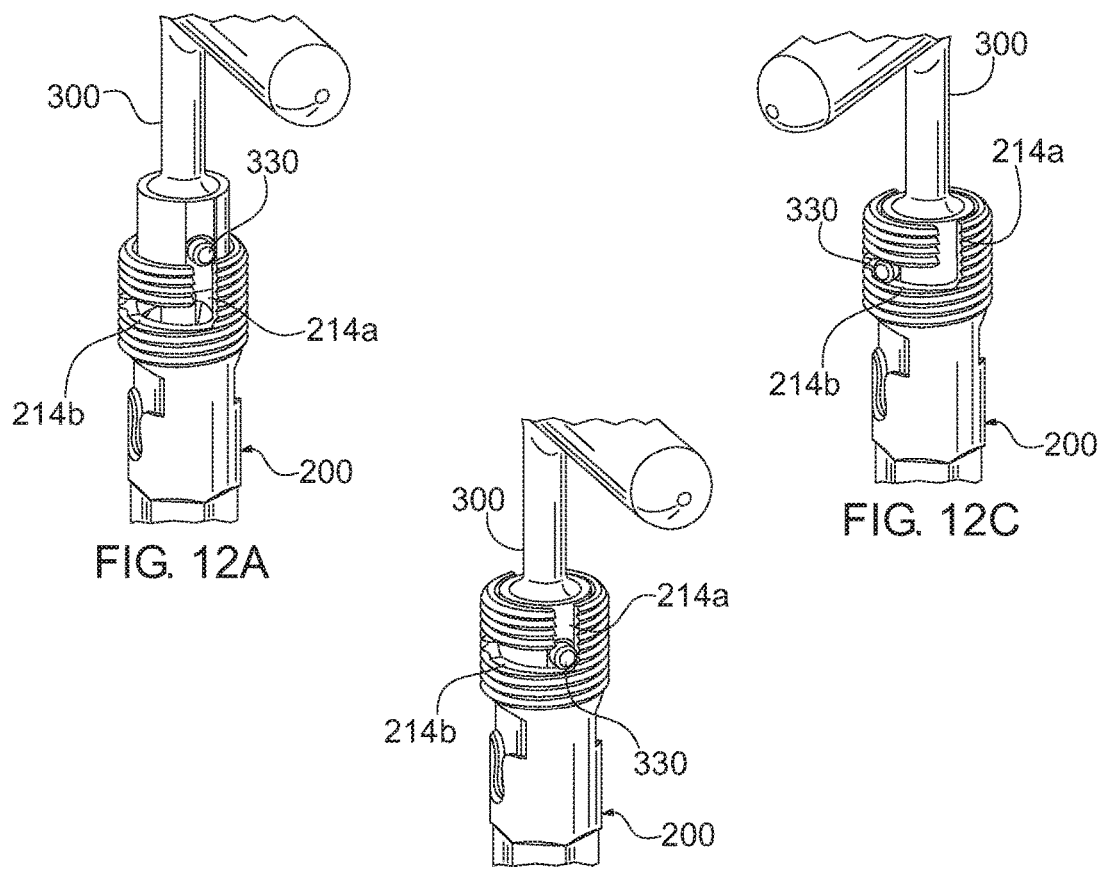
FIG. 12B is a truncated perspective view of the key instrument of FIG. 6 inserted into the downtube of FIG. 3 in a second position.
Figure 12C:
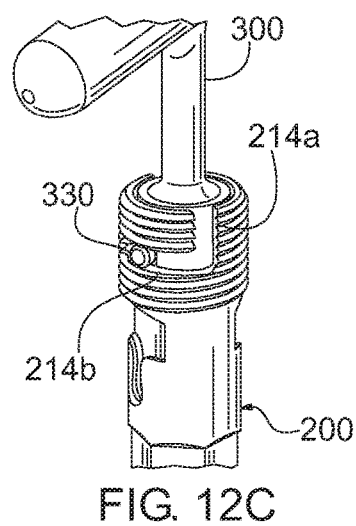
FIG. 12C is a truncated perspective view of the key instrument of FIG. 6 inserted into the downtube of FIG. 3 in a third position.

Referring now to FIGS. 10-12C, key 300 and downtube 200 feature a bayonet locking mechanism that controls the orientation of the key as it is inserted and subsequently rotated in the downtube. Key 300 includes a pair of diametrically opposed tabs 330 in a proximal region of shaft 320 that extend radially outwardly from the shaft. Proximal end 210 of downtube includes a pair of "L"-shaped bayonet slots 214 that are open at the proximal end as shown. The slots 214 are diametrically opposed to one another, and sized to receive tabs 330. Each bayonet slot 214 has a first section 214a parallel to longitudinal axis L and a second section 214b that follows an annular path around downtube 200. The relative positions of the tabs 330 and first sections 214a are such that key 300 can only be inserted into downtube 200 with the engagement end 352 positioned in the clamping orientation relative to the downtube. Once the tabs 330 enter slots 214 and align with second sections 214b, the second sections permit the tabs and key to be rotated clockwise 90 degrees. Once rotated 90 degrees clockwise, the tabs 330 "bottom out" in slots 214, at which point engagement end 352 is positioned between arms 246 in the releasing orientation, to spread apart the arms. FIG. 12A shows the key inserted into downtube 200, with tabs 330 positioned for insertion into slots 214. FIG. 12B shows the key 300 axially advanced further into downtube 200, with tabs 330 bottomed out in the first sections 214a of slots 214. In this position, engagement end 352 is positioned between the arms 246 in the clamping orientation (the clamping orientation being shown in FIG. 8). FIG. 12C shows the key 300 rotated 90 degrees from its position in FIG. 12B, with tabs 330 bottomed out in the second sections 214b of slots 214. In this position, engagement end 352 is positioned between the arms 246 in the releasing orientation (the releasing orientation being shown in FIG. 9).

It is crucial for surgeons to monitor a bone screw as it is being driven into bone. Surgeons must avoid overtightening the screw, which can cause serious damage to the bone. When surgeons insert and tighten bone screws into bone through a downtube, it is difficult to visually monitor the screw to know if it is being overtightened. Therefore, surgeons must rely on "feel" or tactile feedback to monitor their progress in driving the screw into bone. To do this, the screw driver must be rigidly attached to the downtube in a way that minimizes or prevents "play" or toggle between the screw driver and downtube. Even a small amount of toggle between the screw driver and downtube can prevent a surgeon from sensing tactile feedback during a procedure.

Figure 13:
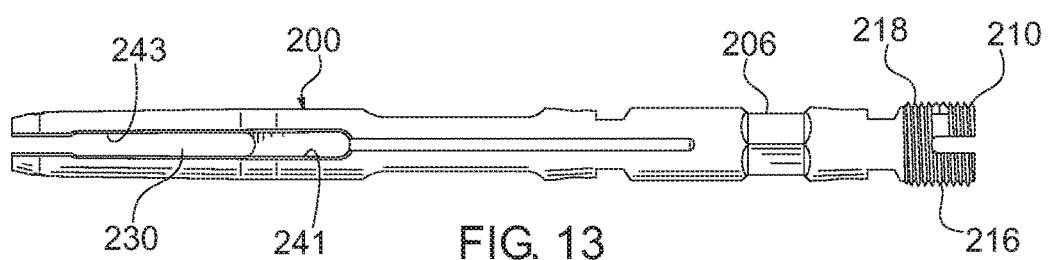
FIG. 13 is a side elevation view of the downtube in FIG. 3.
Figure 14:
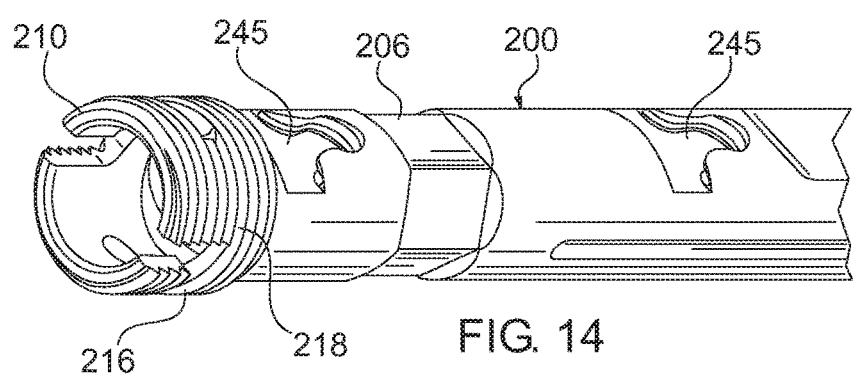
FIG. 14 is an enlarged truncated perspective view of a proximal end of the downtube in FIG. 3.

Preferred downtubes in accordance with the invention include an anti-toggle feature that allows the downtubes to be rigidly attached to other instrumentation. Referring now to FIGS. 13 and 14, proximal end 210 of downtube 200 includes a threaded section 216 with an outer thread 218. Threaded section 216 is configured to mate with different tools after the tools are inserted into the passage 230 of downtube 200, and rigidly hold the tools against toggling as the tools are manipulated inside the downtube.

Figure 15:
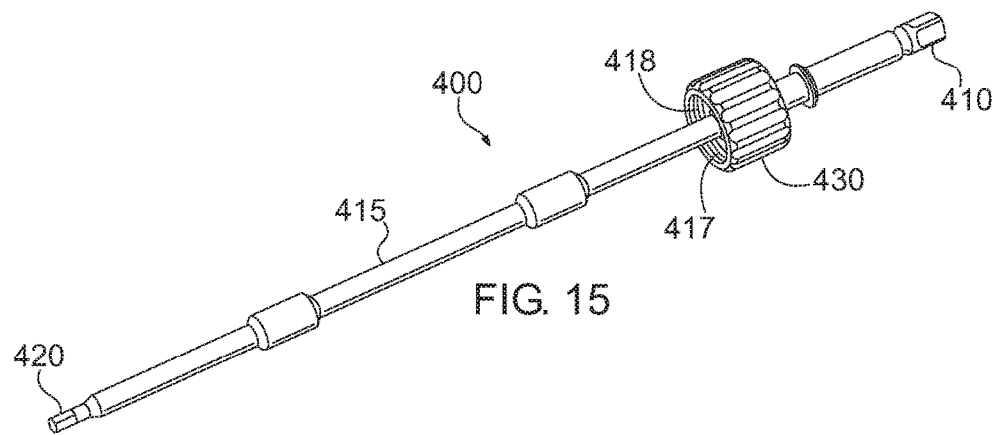
FIG. 15 is a perspective view of a screw driver in accordance with an exemplary embodiment of the invention, for use with the downtube in FIG. 3.
Figure 16:
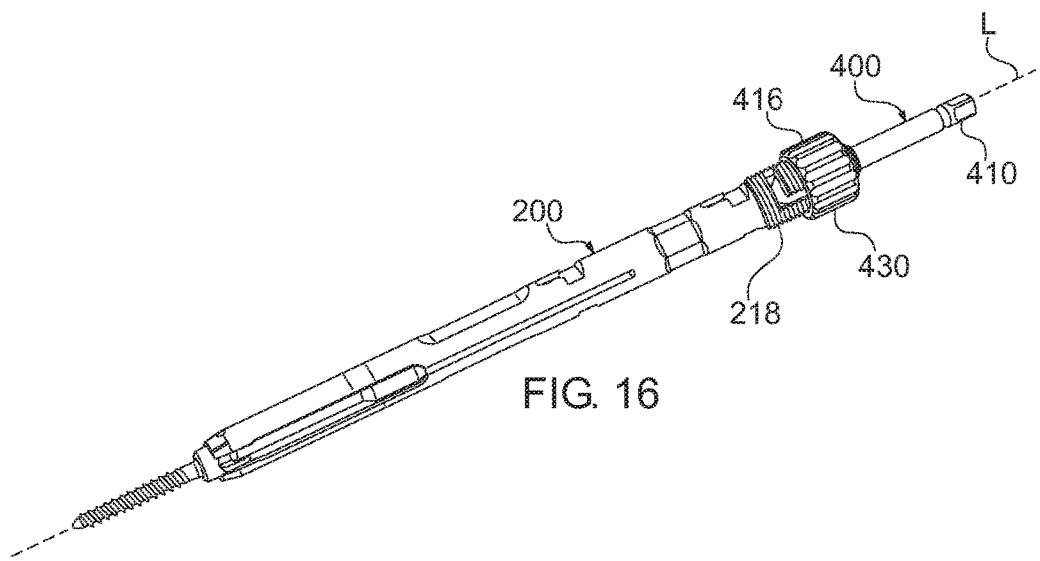
FIG. 16 is a perspective view of the screw driver in FIG. 15 inserted through the downtube in FIG. 3 to engage a screw assembly.

FIGS. 15 and 16 show a screw driver 400 that can be coupled to downtube 200 in accordance with one example. Screw driver 400 includes a proximal end 410, a distal end 420 and a shaft 415 extending between the proximal and distal ends. A hollow cylindrical knob 430 is mounted on shaft 415. Knob 430 is rotatable about shaft 415, and includes a knurled exterior surface 416 and an interior surface 417. Interior surface 417 includes an inner thread 418 adapted to mate with outer thread 218 on downtube 200 as shown. Once screw driver 400 is inserted into passage 230 of downtube 200, knob 430 can be screwed down over the proximal end 210 of the downtube to rigidly attach and lock the screwdriver to the downtube, with no toggle or play. The screw driver shaft 415 is coaxially aligned with the longitudinal axis L of downtube 200, and remains free to rotate relative to the downtube.

Figure 17:
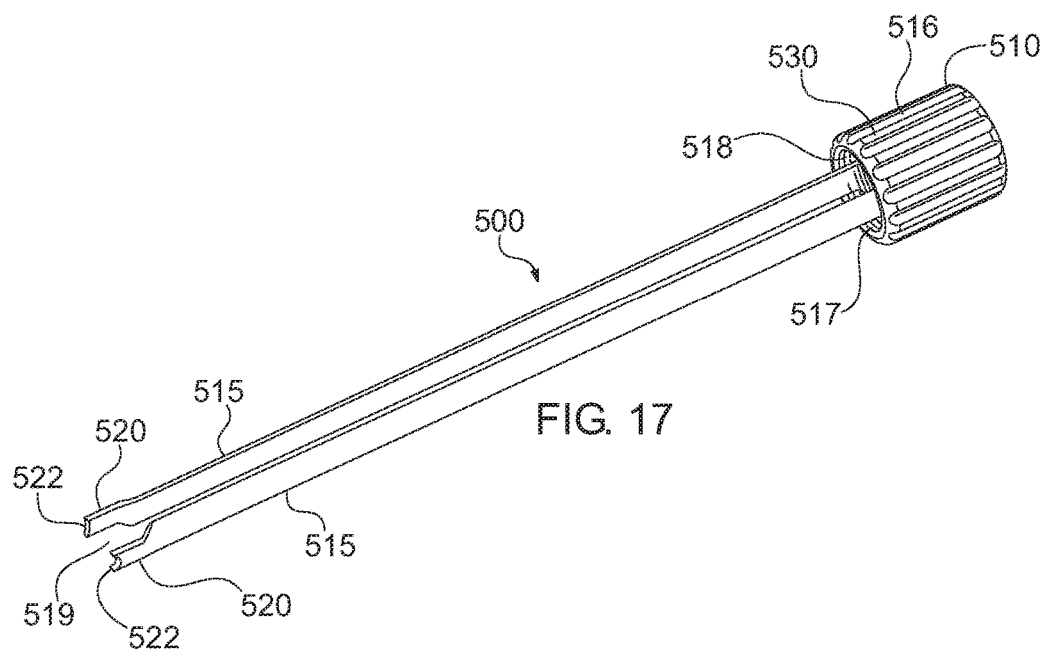
FIG. 17 is a perspective view of a rod persuader in accordance with an exemplary embodiment of the invention, for use with the downtube in FIG. 3.
Figure 18:
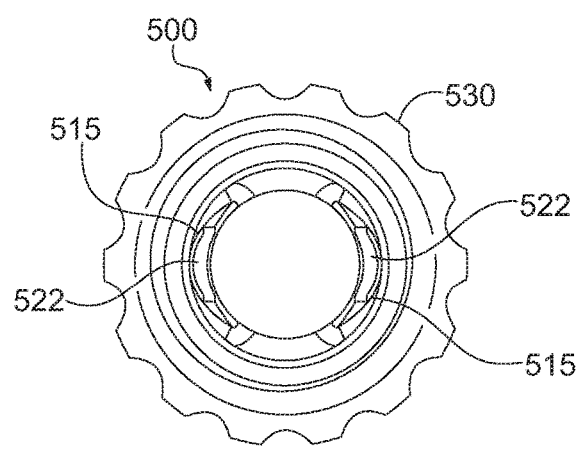
FIG. 18 is an end view of the rod persuader in FIG. 17.
Figure 19:
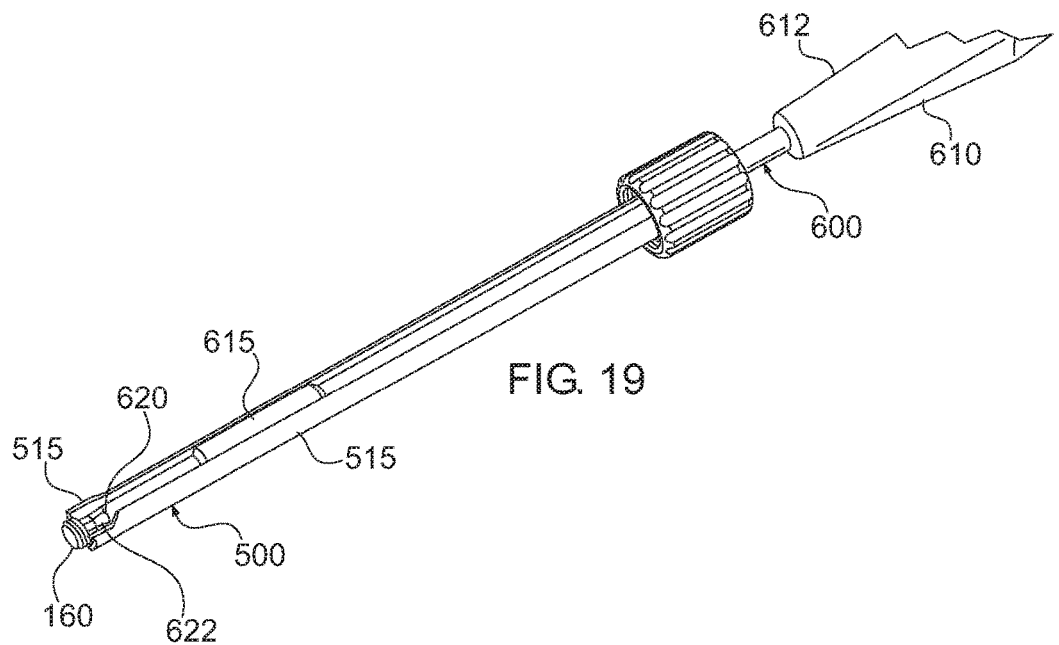
FIG. 19 is a truncated perspective view of the rod persuader in FIG. 17 with a set screw inserter instrument inserted into the rod persuader in accordance with an exemplary embodiment of the invention.
Figure 20:
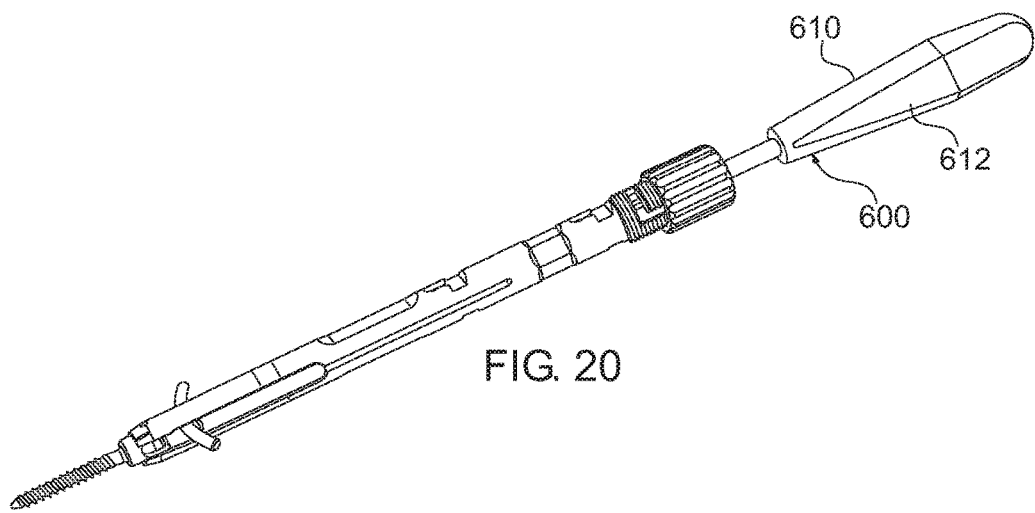
FIG. 20 is a perspective view of the set screw inserter of FIG. 19 inserted into the rod persuader of FIG. 17, which in turn is inserted into the downtube of FIG. 3 to advance a rod into a screw assembly, the rod shown in an unseated position.
Figure 21:
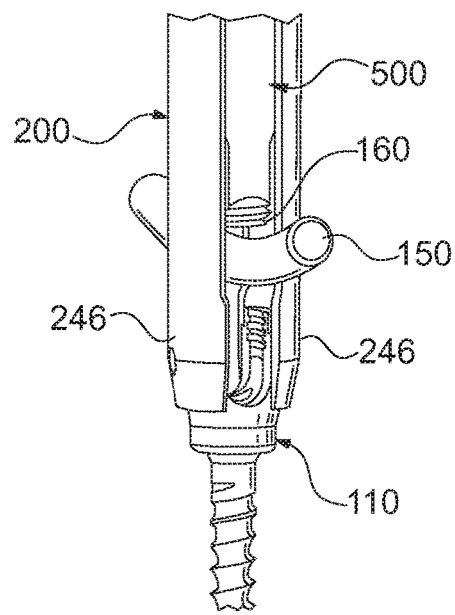
FIG. 21 is an enlarged truncated perspective view of the downtube, rod persuader, set screw inserter, rod and screw assembly in FIG. 20.
Figure 22:
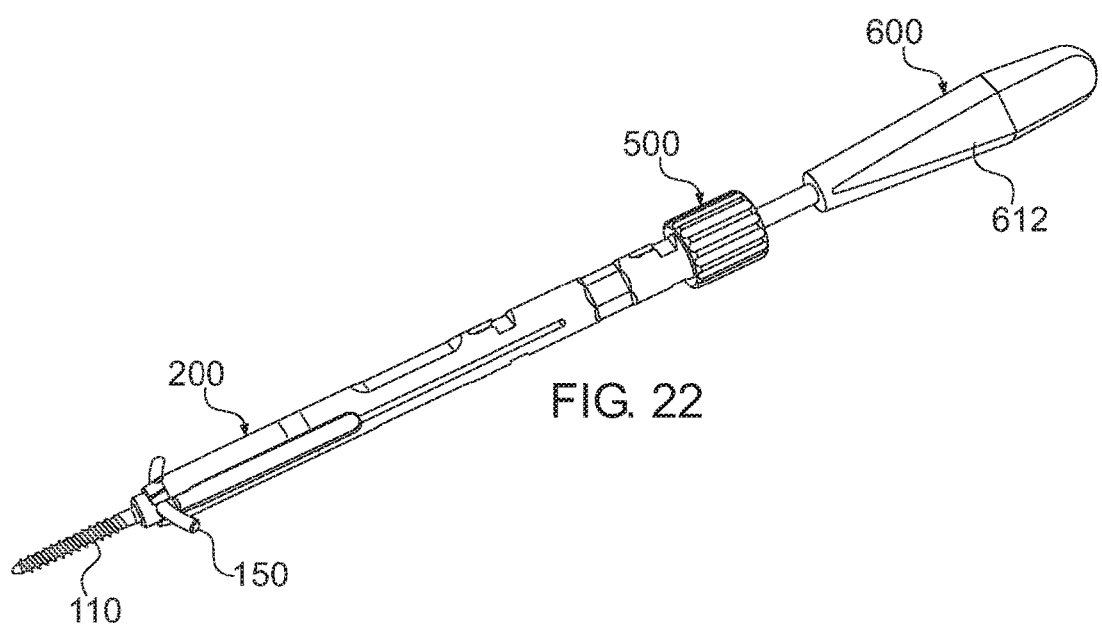
FIG. 22 is a perspective view of the downtube, rod persuader, set screw inserter, rod and screw assembly in FIG. 20, with the rod shown in a seated position.

FIGS. 17 and 18 illustrate a rod persuader 500 that can be coupled to downtube 200 in the same manner described above with respect to screw driver 400. Rod persuader 500 includes a proximal end 510 and a pair of pusher members 515. Pusher members 515 are separated by a central opening 519. Each pusher member 515 has a distal end 520 with a notch 522 to fit around the contour of fixation rod 150. A hollow cylindrical knob 530 is rotatably coupled to the pusher members 515. Knob 530 includes a knurled exterior surface 516 and an interior surface 517. Interior surface 517 includes an inner thread 518 adapted to mate with outer thread 218 on downtube 200. Once rod persuader 500 is inserted into passage 230 of downtube 200, knob 530 can be screwed down over the proximal end 210 of the downtube to rigidly attach the rod persuader to the downtube, with no toggle or play. After knob 530 is threaded onto outer thread 218, the knob can be rotated further to axially advance the pusher members 515 into engagement with rod 150 and push the rod into a desired position in the screw assembly 110.

FIGS. 19-22 show the rod persuader 500 as it could appear when used with a set screw inserter 600 carrying a set screw 160. Set screw inserter 600, which is separate from rod persuader 500, has a proximal end 610 forming a handle 612 and a distal end 620 having a tip 622 that carries the set screw 160. A shaft 615 extends between the proximal end 610 and distal end 620. Set screw inserter 600 may be inserted into downtube 200 after rod persuader 500 is attached to the downtube and engaged with the rod 150. In operation, the set screw inserter 600 is inserted between the pusher members 515 of rod persuader 500, and advanced axially into downtube 200. Set screw inserter 600 is advanced into passage 230 to place set screw 160 into a threaded opening 111 of a screw assembly 110. Once the set screw 160 is properly positioned at the threaded opening 111, handle 612 can be rotated to rotate the shaft 615 and set screw 160 to drive the set screw into the threaded opening of the screw assembly 110.

Downtubes in accordance with the invention may include a number of features on their exterior that cooperate with other instrumentation. Referring back to FIG. 13, for example, downtube 200 includes a pair of diametrically opposed slots 241 and 243 that allow a fixation rod to be maneuvered and inserted into screw assemblies. Slots 241 and 243 are asymmetrical, with slot 241 having a longer length than slot 243. Downtube 200 also includes a hexagonal shaped section 206 configured for engagement with a counter-torque instrument. Downtube 200 further includes a pair of T-shaped slots 245, shown best in FIG. 14, for the attachment of different instruments, including but not limited to compressor and distraction instruments, and cross bars for preventing relative movement between adjacent downtubes. Slots 245 act as receivers for round studs (not shown) that are T-shaped in cross section. After being slid into place, the studs allow load to be applied to the tube to apply a compression and distraction force to the screw assemblies.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. An instrument assembly for providing access to a bone anchor, the instrument assembly comprising:
 a downtube having a tubular body with a proximal end and a distal end, the proximal end forming an opening for receiving a surgical tool, and the distal end forming at least two attachment members for attaching to a bone anchor, the tubular body forming a hollow passage extending from the proximal end to the distal end, the hollow passage defining an elliptical or oval shaped section, the downtube including diametrically opposed slots that are asymmetrical with respect to one another; and
 a key for insertion into the proximal end of the downtube to attach the downtube to a bone anchor, the key comprising an elliptical or oval shaped engagement end, the engagement end configured to engage the at least two attachment members when the elliptical or oval shaped engagement end is positioned in the elliptical or oval shaped section of the passage, the key rotatable within the tubular body between a clamping orientation, in which the at least two attachment members are separated from one another by a first distance, and a releasing orientation, in which the elliptical or oval shaped engagement end bears outwardly against the at least two attachment members and separates the at least two attachment members from one another by a second distance greater than the first distance.

2. The instrument assembly of claim 1, wherein each of the at least two attachment members comprises an arm having a bearing surface facing into the passage of the downtube.

3. The instrument assembly of claim 2, wherein each arm comprises a tab extending inwardly into the passage.

4. The instrument assembly of claim 3, wherein the tabs are diametrically opposed to one another.

5. The instrument assembly of claim 3, wherein the tabs are circular.

6. The instrument assembly of claim 1, wherein the key comprises a shaft with at least one tab extending radially outwardly from the shaft.

7. The instrument assembly of claim 6, wherein the proximal end of the tubular body comprises a bayonet slot adapted to receive the at least one tab on the key.

8. The instrument assembly of claim 7, wherein the key is rotatable within the tubular body when the tab is positioned in the bayonet slot, the bayonet slot limiting movement of the tab to limit rotation of the key within the tubular body between the clamping position and the releasing position.

9. The instrument assembly of claim 8, wherein the proximal end of the tubular body comprises a threaded section with an outer thread.

10. The instrument assembly of claim 9, wherein the bayonet slot extends through the threaded section of the proximal end.

11. The instrument assembly of claim 9, further comprising a screwdriver, the screwdriver comprising a shaft and a hollow knob that circumscribes the shaft of the screwdriver, the knob rotatable relative to the shaft of the screwdriver and comprising an inner thread configured to engage the outer thread on the tubular body to connect the screwdriver to the downtube in a coaxial relationship.

12. The instrument assembly of claim 9, further comprising a rod persuader, the rod persuader comprising a pair of pusher members and a hollow knob that circumscribes the pusher members, the knob rotatable relative to the pusher members and comprising an inner thread configured to engage the outer thread on the tubular body to connect the rod persuader to the downtube with the pusher members extending inside the tubular body.

13. The instrument assembly of claim 12, wherein the rod persuader forms a central opening between the pusher members.

14. The instrument assembly of claim 13, further comprising a set screw inserter, the set screw inserter comprising a shaft configured for insertion into the central opening of the rod persuader while the rod persuader is inserted into the tubular body.

15. The instrument assembly of claim 14, wherein the set screw inserter comprises a distal end and a set screw releasably attached to the distal end of the set screw inserter.

16. The instrument assembly of claim 1, wherein the tubular body of the downtube comprises a hexagonal shaped midsection configured for engagement with a counter-torque instrument.

17. The instrument assembly of claim 1, wherein the diametrically opposed slots comprise a first slot having a first length and a second slot having a second length, the first length being longer than the second length.

18. An instrument assembly for providing access to a bone anchor, the instrument assembly comprising:
 a downtube having a tubular body with a proximal end, a distal end and a longitudinal axis, the proximal end forming an opening for receiving a surgical tool, and the distal end forming at least two attachment members for attaching to the bone anchor, the tubular body forming a hollow passage extending from the proximal end to the distal end, the hollow passage defining an elliptical or oval shaped section; and a key for clamping and unclamping the downtube to the bone anchor, the key being insertable into the proximal end of the downtube and comprising an elliptical or oval shaped engagement end, the engagement end configured to engage the at least two attachment members when the engagement end is positioned in the elliptical or oval shaped section of the passage, the engagement end being rotatable within the tubular body between a clamping orientation, in which the engagement end separates the at least two attachment members from one another by a first distance, and a releasing orientation, in which the engagement end bears outwardly against the at least two attachment members and separates the at least two attachment members from one another by a second distance greater than the first distance, the key comprising a shaft and a tab extending radially outwardly from the shaft, the proximal end of the tubular body of the downtube defining a bayonet slot adapted to receive the tab on the key, the bayonet slot defining a first section extending parallel to the longitudinal axis of the tubular body that is open at the proximal end of the tubular body, and a second section that follows an annular path around the tubular body, the tab, the first section of the bayonet slot, and the second section of the bayonet slot being positioned relative to one another such that when the key is initially inserted into the downtube, with the tab received in the first section of the bayonet slot, the engagement end is oriented in the clamping orientation, and when the key is rotated in the downtube, with the tab moved into the second section of the bayonet slot, the engagement end is oriented in the releasing orientation.

* * * * *